US00PP09995P

United States Patent [19]

Svejda et al.

[11] Patent Number: Plant 9,995

[45] Date of Patent: Aug. 12, 1997

[54] CLIMBING ROSE PLANT NAMED 'QUADRA'

[75] Inventors: Felicitas J. Svejda, Nepean; Ian S. Ogilvie, Pointe Claire, both of Canada

[73] Assignee: Her Majesty the Queen in right of Canada, as represented by the Minister of Agriculture, Ontario, Canada

[21] Appl. No.: 661,097

[22] Filed: Jun. 10, 1996

[51] Int. Cl.[6] ..... A01H 5/00

[52] U.S. Cl. ..... Plt./6

[58] Field of Search ..... Plt./1, 2, 6, 7.1, Plt./10, 22, 28, 29

*Primary Examiner*—Howard J. Locker

*Attorney, Agent, or Firm*—Burns, Doane, Swecker & Mathis, L.L.P.

[57] ABSTRACT

A new and distinct variety of climbing rose plant is provided which forms in clusters attractive deep red blossoms that tend to lighten somewhat when fully open. The new variety exhibits a spreading or trailing growth habit with glossy dark green foliage, and good winter hardiness. The newly opened leaves commonly display an attractive red tinge. Resistance to powdery mildew and blackspot has been observed. The new variety propagates well by the use of softwood stem cuttings, and is well adapted for growing as colorful ornamentation in the landscape.

2 Drawing Sheets

SUMMARY OF THE INVENTION

The new variety of climbing rose plant of the present invention was created by artificial pollination at the Central Experimental Farm, Ottawa, Ontario, Canada. The female parent (i.e., the seed parent) was the B08 line (non-patented in the United States) and the male parent (i.e., the pollen parent) was the U11 line (non-patented in the United States). The B08 line was a complex hybrid between tender and hardy lines and the U11 line was a hardy pink climber. The B08 line was derived from a cross between A15 (non-patented in the United States), a hybrid of 'Queen Elizabeth' (U.S. Plant Pat. No. 1,259) and 'Arthur Bell' (non-patented in the United States) and D36 (non-patented in the United States), a hybrid between an unregistered breeding line developed by Robert Simonet of Alberta, Canada, and the German shrub rose, 'Von Scharnhorst' (non-patented in the United States). The U11 line was derived from an open-pollinated seedling 'Red Dawn' that originated from the cross of the climber 'New Dawn' (non-patented in the United States) and 'Suzanne' (non-patented in the United States). 'Suzanne' was a hybrid of *Rosa laxa* Retz. and *Rosa spinosissima* L. The breeding program was designed to impart a high degree of winter hardiness to the offspring.

It was found that the new variety of climbing rose plant of the present invention possesses the following combination of characteristics:

(a) exhibits a spreading or trailing growth habit with attractive dark green glossy foliage wherein the newly opened leaves commonly display a red tinge,
(b) forms in clusters attractive deep red blossoms that tend to lighten when fully open,
(c) propagates well by the use of softwood cuttings,
(d) exhibits a good winter hardiness, and
(e) is particularly well suited for growing as ornamentation in the landscape.

The rose plants can be grown well on their own roots out-of-doors without protection at L'Assomption, Quebec, Canada. The blossoms commonly appear in large quantities during June and repeat throughout the summer to late September. Resistance to powdery mildew and blackspot has been exhibited.

While the new variety resembles 'John Davis' (non-patented in the United States) and 'William Baffin' (non-patented in the United States), it can be readily distinguished by its many petalled deep red flowers that make it unique among hardy climbers.

The new variety well meets the needs of the horticultural industry. It can be grown to advantage as attractive ornamentation in parks, gardens, public areas, and residential landscapes. It is particularly well suited for growing in the landscape.

The characteristics of the new variety have been found to be homogenous and stable and have been shown to be strictly transmissible by asexual propagation by the rooting of softwood stem cuttings conducted at L'Assomption, Quebec, Canada.

The new variety has been named the 'Quadra'.

BRIEF DESCRIPTION OF THE PHOTOGRAPHS

The accompanying photographs show, as nearly true as it is reasonably possible to make the same in color illustrations of this character, typical specimens of plants and plant parts of the new variety. The rose plants of the new variety described herein were approximately 5 to 6 years of age and were photographed while growing on their own roots at L'Assomption, Quebec, Canada.

DETAILED DESCRIPTION

Figure 1:
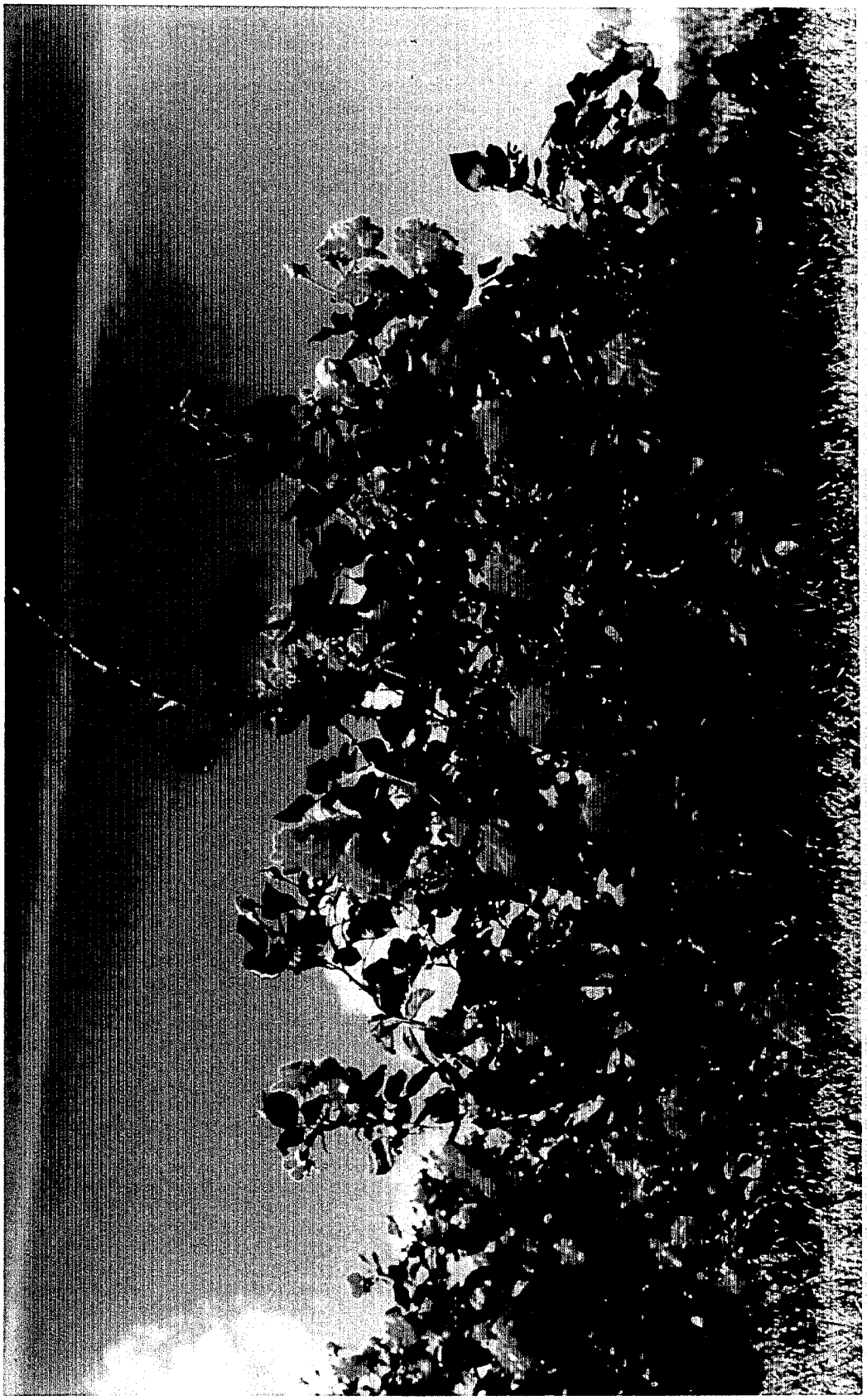
FIG. 1 illustrates a typical flowering plant of the new variety while growing in the landscape. The spreading or trailing habit, abundant foliage, and dark red blossoms are apparent.
Figure 2:
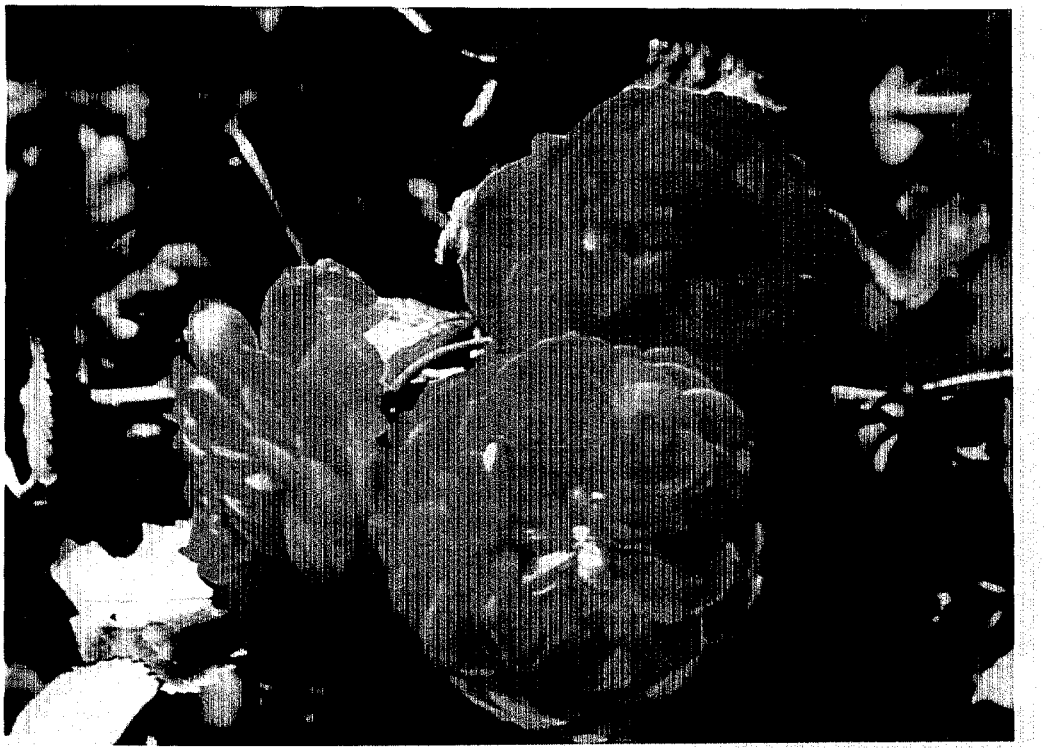
FIG. 2 illustrates typical blossoms and foliage of the new variety.

The chart used in the identification of colors is that of The Royal Horticultural Society (R.H.S. Colour Chart). Common color terms are to be accorded their ordinary dictionary significance. The description is based on the observation of 5 to 6 year-old plants of the new variety while being grown outdoors at L'Assomption, Quebec, Canada.

Class: Climbing.

Plant:

*Height.*—A five year-old plant commonly assumes a height of approximately 0.1±0.2 m.

*Width.*—A five year-old plant commonly assumes a width of approximately 1.8±0.3 m.

*Habit.*—Spreading or trailing.

Thorns:

*Quantity.*—Approximately 10±2 thorns per 100 mm. of stem on average.

Leaves: Compound and pinnate.

*Leaflets.*—Number: commonly 3, 5 or 7. Frequency: abundant. Shape: ovate and acuminate. Size: approximately 45±5 mm. in length on average, and approximately 25±3 mm. in width on average. Margins: dentate.

*Color.*—Adult foliage: dark green, Yellow-Green Group 147A with a red tinge of Red Group 46A on upper surface. Such red tinge which develops on newly opened leaves adds to the attractiveness of the plant. Texture: leathery. General appearance: dark green, and glossy.

Inflorescence:

*Number of flowers.*—Commonly in clusters of 1 to 4.

*Peduncle.*—Generally erect.

*Buds.*—Shape: ovoid before the opening of the sepals. Color upon opening: the outer petals are deep red, Red Group 46A when unopened.

*Flower.*—Shape: assume a more flattened configuration when fully open (as illustrated). Diameter: approximately 80±10 mm. on average. Color (when blooming): deep red, Red Group 46A on the upper surface and Red Group 46D on the under surface. The upper surface coloration of the blossoms commonly fades to Red Group 46D when the blossoms are fully mature. The petals have a white spot at the base. Fragrance: slight. Petal number: approximately 66±4 on average. Petal drop: petals tend to detach fairly clearly. Fertility: flowers commonly possess a low level of fertility and only occasional hips are formed. Lasting quality: the blossoms commonly last 3 to 5 days when cut and placed in a vase and generally last longer on the plant. The blossom life is influenced by temperature and other environmental conditions that are encountered.

Development:

*Vegetation.*—Good vigor.

*Blossoming.*—In large quantities during June with repetition throughout the summer to late September.

*Hardiness.*—Has survived test winters to −35° C. without protection except for natural snow with only slight tip kill on younger shoots.

*Resistance to diseases.*—A high resistance to powdery mildew [*Sphaerotheca pannosa* (Wallr. ex Fr.) Lev.] and blackspot (*Diplocarpon rosae* Wolf.) has been observed.

*Preferred mode of propagation.*—The use of softwood cuttings to produce self-rooted plants is recommended. For instance, softwood cuttings taken at the bud stage can be dipped in rooting powder (e.g., Stimroot No. 2, 0.4 percent indolebutyric acid of Plant Products, Bramalea, Ontario, Canada) and placed under mist for 3 to 4 weeks at 20° to 25° C. ambient temperature.

We claim:

1. A new and distinct variety of climbing rose plant characterized by the following combination of characteristics:

(a) exhibits a spreading or trailing growth habit with attractive dark green glossy foliage wherein the newly opened leaves commonly display a red tinge,
(b) forms in clusters attractive deep red blossoms that tend to lighten when fully open,
(c) propagates well by the use of softwood cuttings,
(d) exhibits a good winter hardiness, and
(e) is particularly well suited for growing as ornamentation in the landscape;

substantially as herein shown and described.

* * * * *